US011348050B2

(12) United States Patent
Fargis

(10) Patent No.: US 11,348,050 B2
(45) Date of Patent: May 31, 2022

(54) METHODS FOR OPTIMIZING ANALYSIS OF RISK MANAGEMENT DATA AND DEVICES THEREOF

(71) Applicant: Professional Risk Associates, Inc., Midlothian, VA (US)

(72) Inventor: Stephen S. Fargis, Richmond, VA (US)

(73) Assignee: PROFESSIONAL RISK ASSOCIATES, INC., Midlothian, VA (US)

( * ) Notice: Subject to any disclaimer, the term of this patent is extended or adjusted under 35 U.S.C. 154(b) by 703 days.

(21) Appl. No.: 14/724,912

(22) Filed: May 29, 2015

(65) Prior Publication Data

US 2015/0363719 A1 Dec. 17, 2015

Related U.S. Application Data

(60) Provisional application No. 62/012,749, filed on Jun. 16, 2014.

(51) Int. Cl.
| | |
|---|---|
| *G16H 15/00* | (2018.01) |
| *G06Q 10/06* | (2012.01) |
| *G06Q 40/08* | (2012.01) |
| *G16H 70/60* | (2018.01) |

(52) U.S. Cl.
CPC ......... *G06Q 10/0635* (2013.01); *G06Q 40/08* (2013.01); *G16H 15/00* (2018.01); *G16H 70/60* (2018.01)

(58) Field of Classification Search
CPC ............ G06Q 50/22–24; G06Q 40/08; G06Q 10/0635; G06F 19/30
See application file for complete search history.

(56) References Cited

U.S. PATENT DOCUMENTS

| | | | |
|---|---|---|---|
| 6,266,645 B1 * | 7/2001 | Simpson ................ | G06Q 10/10 705/3 |
| 6,615,181 B1 * | 9/2003 | Segal ..................... | G06Q 40/08 705/4 |

(Continued)

*Primary Examiner* — Robert A Sorey
(74) *Attorney, Agent, or Firm* — Troutman Pepper Hamilton Sanders LLP (Rochester)

(57) ABSTRACT

A method, non-transitory computer readable medium, and risk analyzing computing device that obtains condition indication data associated with a medical practice and comprising a plurality of condition indications, a type of the medical practice, and, from a medical malpractice claims source database and via one or more communication networks, medical malpractice claims data for a plurality of medical liability insurance carriers. The condition indication data is compared to the medical malpractice claims data to identify one or more of a plurality of risk issues associated in the medical malpractice claims data with a predetermined number of highest ranked one or more of the condition indications in the condition indication data. One or more recommended risk management interventions associated with the one or more risk issues are provided to the medical practice. Accordingly, this technology efficiently and effectively provides risk management interventions that are aligned with medical practice specialties.

12 Claims, 7 Drawing Sheets
(5 of 7 Drawing Sheet(s) Filed in Color)

(56) References Cited

U.S. PATENT DOCUMENTS

| | | | | |
|---|---|---|---|---|
| 8,543,429 B1* | 9/2013 | Milanovich | ............ | G06Q 10/10 |
| | | | | 705/4 |
| 2004/0064341 A1* | 4/2004 | Langan | ................ | G06F 19/324 |
| | | | | 705/2 |
| 2004/0107121 A1* | 6/2004 | Segal | .................... | G06Q 40/08 |
| | | | | 705/4 |
| 2004/0267579 A1* | 12/2004 | Markman | ............. | G06Q 40/08 |
| | | | | 705/4 |
| 2007/0239490 A1* | 10/2007 | Sullivan | ............. | G06F 19/3406 |
| | | | | 705/3 |
| 2009/0132295 A1* | 5/2009 | Pecan | ................... | G06Q 40/08 |
| | | | | 705/4 |
| 2012/0130745 A1* | 5/2012 | Jones | ................... | G06F 19/327 |
| | | | | 705/3 |
| 2014/0358587 A1* | 12/2014 | Cao | ....................... | A61B 5/747 |
| | | | | 705/3 |

* cited by examiner

| CONDITION/TOP MISADVENTURES | CLOSED CLAIMS | PAID CLAIMS | % PAID-TO-CLOSED | AVG INDEMNITY | AVG ALAE |
|---|---|---|---|---|---|
| V76.12 - Oth Screening Mammogram | 190 | 106 | 55.8 | $435,924 | $34,566 |
| Errors in diagnosis | 114 | 81 | 71.1 | $420,262 | $33,488 |
| Failure to supervise or monitor case | 11 | 11 | 100.0 | $387,727 | $44,381 |
| 786.5 - Unspec Chest Pain | 149 | 32 | 21.5 | $344,812 | $26,010 |
| Errors in diagnosis | 80 | 21 | 26.3 | $403,416 | $26,976 |
| Failure to supervise or monitor case | 7 | 3 | 42.9 | $358,250 | $44,839 |
| 789 - Abdominal Pain, Unspec Site | 252 | 66 | 26.2 | $255,499 | $30,409 |
| Errors in diagnosis | 119 | 43 | 36.1 | $302,715 | $27,407 |
| Improper performance | 36 | 11 | 30.6 | $128,828 | $37,246 |
| 786.05 - Shortness of Breath | 34 | 8 | 23.5 | $329,313 | $25,377 |
| 729.5 - Pain in Limb | 84 | 29 | 34.5 | $212,276 | $20,986 |
| 786.2 - Cough | 45 | 15 | 33.3 | $342,722 | $17,333 |
| 784 - Headache | 146 | 50 | 34.2 | $586,845 | $29,422 |
| Errors in diagnosis | 69 | 35 | 50.7 | $769,245 | $44,242 |
| Improper performance | 20 | 8 | 40.0 | $92,252 | $13,077 |
| 729.81 - Swelling of Limb | 19 | 2 | 10.5 | $115,000 | $14,417 |
| V58.82 - Fitting and Adjustment of Non-vasc Catheter, Oth | - | - | - | $0 | $0 |
| 959.7 - Oth Unspec Injury to Knee, Leg, Ankle and Foot | 75 | 25 | 33.3 | $58,950 | $16,586 |

| CONDITION/TOP PROCEDURES | CLOSED CLAIMS | PAID CLAIMS | % PAID-TO-CLOSED | AVG INDEMNITY | AVG ALAE |
|---|---|---|---|---|---|
| V76.12 - Oth Screening Mammogram | 190 | 106 | 55.8 | $435,924 | $34,566 |
| Mammography | 170 | 95 | 55.9 | $418,199 | $34,843 |
| Diagnostic interview, evaluation, or consultation | 9 | 7 | 77.8 | $643,572 | $38,053 |
| 786.5 - Unspec Chest Pain | 149 | 32 | 21.5 | $344,812 | $26,010 |
| Chest x-ray | 66 | 10 | 15.2 | $546,978 | $29,695 |
| Computerized axial tomography (CAT scan) | 16 | 4 | 25.0 | $444,521 | $23,611 |
| Diagnostic interview, evaluation, or consultation | 10 | 4 | 40.0 | $205,250 | $26,771 |
| Nuclear medicine and radioisotopic studies | 7 | 4 | 57.1 | $156,875 | $34,858 |
| 789 - Abdominal Pain, Unspec site | 252 | 66 | 26.2 | $255,499 | $30,409 |
| Computerized axial tomography (CAT scan) | 71 | 19 | 26.8 | $557,167 | $35,976 |
| Diagnostic radiologic procedures, using contrast material | 23 | 11 | 47.8 | $120,637 | $22,266 |
| 786.05 - Shortness of Breath | 34 | 8 | 23.5 | $329,313 | $25,377 |
| 729.5 - Pain in Limb | 84 | 29 | 34.5 | $212,276 | $20,986 |
| 786.2 - Cough | 45 | 15 | 33.3 | $342,722 | $17,333 |
| 784 - Headache | 146 | 50 | 34.2 | $586,845 | $29,422 |
| Computerized axial tomography (CAT scan) | 71 | 23 | 32.4 | $684,857 | $31,028 |
| Magnetic resonance imaging | 21 | 12 | 57.1 | $451,683 | $23,581 |
| 729.81 - Swelling of Limb | 19 | 2 | 10.5 | $115,000 | $14,417 |
| V58.82 - Fitting and Adjustment of Non-vasc Catheter, Oth | - | - | - | $0 | $0 |
| 959.7 - Oth Unspec Injury to Knee, Leg, Ankle and Foot | 75 | 25 | 33.3 | $58,950 | $16,586 |

| CONDITION/TOP ASSOCIATED ISSUES (EXCLUDING OTHER AND NONE) | CLOSED CLAIMS | PAID CLAIMS | % PAID-TO-CLOSED | AVG INDEMNITY | AVG ALAE |
|---|---|---|---|---|---|
| V76.12 - Oth Screening Mammogram | 190 | 106 | 55.8 | $435,924 | $34,566 |
| Problems with a patient's history, exam or work-up | 15 | 10 | 66.7 | $424,950 | |
| X-ray Error | 13 | 10 | 76.9 | $456,750 | $26,010 |
| 786.5 - Unspec Chest Pain | 149 | 32 | 21.5 | $344,812 | |
| X-ray Error | 8 | 4 | 50.0 | $202,851 | |
| Vicarious Liability | 7 | 2 | 28.6 | $325,000 | |
| 789 - Abdominal Pain, Unspec Site | 252 | 66 | 26.2 | $255,499 | $30,409 |
| X-ray Error | 23 | 10 | 43.5 | $124,383 | |
| Unnecessary Treatment | 7 | 4 | 57.1 | $102,893 | |
| 786.03 - Shortness of Breath | 34 | 8 | 23.5 | $329,313 | $25,377 |
| 729.5 - Pain in Limb | 84 | 29 | 34.5 | $212,276 | $20,986 |
| 786.2 - Cough | 45 | 15 | 33.3 | $342,722 | $17,333 |
| 784 - Headache | 146 | 50 | 34.2 | $586,845 | $29,422 |
| X-ray Error | 13 | 8 | 61.5 | $362,203 | |
| Vicarious Liability | 4 | 3 | 75.0 | $59,167 | |
| 729.81 - Swelling of Limb | 19 | 2 | 10.5 | $115,000 | $14,417 |
| V58.82 - Fitting and Adjustment of Non-vasc Catheter, Oth | - | - | - | $0 | $0 |
| 959.7 - Oth Unspec Injury to Knee, Leg, Ankle and Foot | 75 | 25 | 33.3 | $58,950 | $16,586 |

METHODS FOR OPTIMIZING ANALYSIS OF RISK MANAGEMENT DATA AND DEVICES THEREOF

This application claims the benefit of U.S. Provisional Patent Application Ser. No. 62/012,749, filed on Jun. 16, 2014, which is hereby incorporated by reference in its entirety.

FIELD

This technology relates to methods and devices for optimizing analysis of risk management data for medical practices.

BACKGROUND

Medical practices are often exposed to significant risks in the treatment of patients and generally carry insurance and undertake risk management interventions and mitigation efforts in order to manage the risk. Risk management computing devices have utilized risk management algorithms on bulk or generalized risk management data to provide risk management data analysis for medical practices in order to minimize financial liability risk.

Unfortunately, both medical practices and risk management providers typically utilize separate and distinct computing technologies. Accordingly, risk management computing devices execute analytics on risk management data that is separate from practice data maintained by medical practice computing devices and specific to medical practices for which a risk management program may be directed.

Therefore, risk management programs and services for medical practices are often not structured based on, or correlated with, the specialized treatments provided by the medical practices. As yet, there has been no effective way to facilitate a directed approach to risk management, and to thereby reduce risk and associated insurance costs as well as improve patient care and safety.

SUMMARY

A method for providing risk management analytic data includes obtaining condition indication data associated with a medical practice and comprising a plurality of condition indications, a type of the medical practice, and, from a medical malpractice claims source database and via one or more communication networks, medical malpractice claims data for a plurality of medical liability insurance carriers. The condition indication data is compared to the medical malpractice claims data to identify one or more of a plurality of risk issues associated in the medical malpractice claims data with a predetermined number of highest ranked one or more of the condition indications in the condition indication data. One or more of the recommended risk management interventions associated with the one or more risk issues are provided to the medical practice.

A non-transitory computer readable medium having stored thereon instructions for providing risk management analytics comprising executable code which when executed by a processor, causes the processor to perform steps including obtaining condition indication data associated with a medical practice and comprising a plurality of condition indications, a type of the medical practice, and, from a medical malpractice claims source database and via one or more communication networks, medical malpractice claims data for a plurality of medical liability insurance carriers. The condition indication data is compared to the medical malpractice claims data to identify one or more of a plurality of risk issues associated in the medical malpractice claims data with a predetermined number of highest ranked one or more of the condition indications in the condition indication data. One or more of the recommended risk management interventions associated with the one or more risk issues are provided to the medical practice.

A risk analyzing computing device, comprising at least one processor and a memory coupled to the processor which is configured to be capable of executing programmed instructions comprising and stored in the memory to obtain condition indication data associated with a medical practice and comprising a plurality of condition indications, a type of the medical practice, and, from a medical malpractice claims source database and via one or more communication networks, medical malpractice claims data for a plurality of medical liability insurance carriers. The condition indication data is compared to the medical malpractice claims data to identify one or more of a plurality of risk issues associated in the medical malpractice claims data with a predetermined number of highest ranked one or more of the condition indications in the condition indication data. One or more of the recommended risk management interventions associated with the one or more risk issues are provided to the medical practice.

This technology provides a number of advantages including methods, non-transitory computer readable media, and devices that facilitate integration in computer technologies of the identification and analysis of risk management data for medical practices with the executed medical practice analytics for improving patient care and safety. For example, with this technology medical malpractice claims data for numerous medical practices is advantageously compared to medical practice data to identify risk issues associated with machine condition indications, such as ICD-9 codes, in the data. Accordingly, through the integration of these previously separate computer technologies patient outcomes can be increased, pay for performance results can be improved, and insurance costs can be reduced.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 is an exemplary table of medical malpractice claims data including misadventure risk issues for the top ten condition indicators for a radiology type of medical practice;

FIG. 4 is an exemplary table of medical malpractice claims data including procedure risk issues for the top ten condition indicators for a radiology type of medical practice;

FIG. 5 is an exemplary table of medical malpractice claims data including legal risk issues for the top ten condition indicators for a radiology type of medical practice;

DETAILED DESCRIPTION

Figure 1:
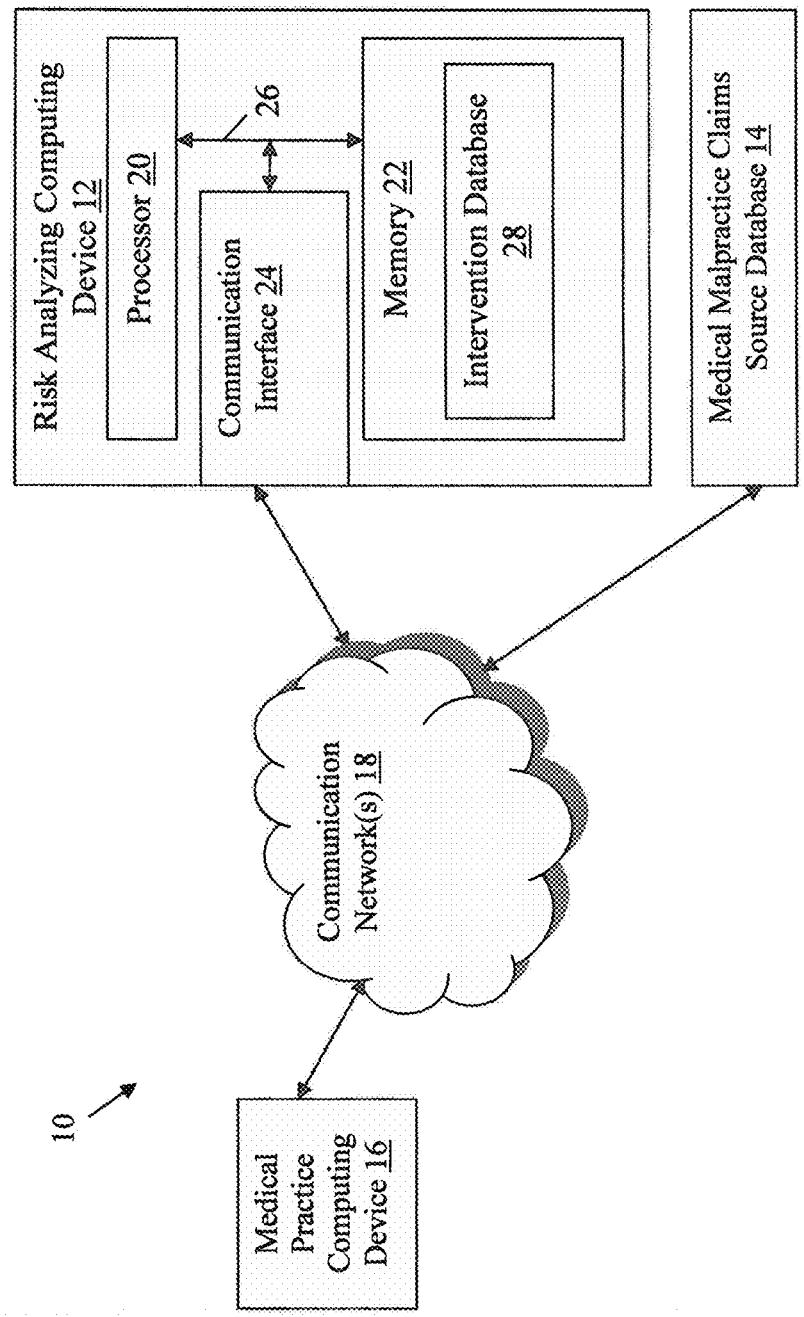
FIG. 1 is a block diagram of a network environment with an exemplary risk analyzing computing device.

An exemplary network environment 10 with a risk analyzing computing device 12, medical malpractice claims source database 14, and a medical practice computing device 16 is illustrated in FIG. 1. In this example, one or more of the risk analyzing computing device 12, medical malpractice claims source database 14, and medical practice computing device 16 are optionally capable of communicating over the communication network(s) 18. This technology provides a number of advantages including methods, non-transitory computer readable media, and devices that facilitate integration in computer technologies of the identification and analysis of risk management data for medical practices with the executed medical practice analytics for improving patient care and safety.

The risk analyzing computing device 12 in this example may perform any number of functions including facilitating the comparing and analyzing of medical malpractice claims data received from medical practices and corresponding condition indications for one medical practice to provide targeted risk management intervention recommendations, for example. In this example, the risk analyzing computing device 12 includes a processor 20, a memory 22, and a communication interface 24, which are connected by a bus 26 or other communication link.

The processor 20 in the risk analyzing computing device 12 executes instructions for one or more aspects of this technology, as described and illustrated by way of the embodiments herein, although the processor 20 could execute other numbers and types of programmed instructions. The memory 22 in the risk analyzing computing device 12 stores these instructions for one or more aspects of this technology, as described and illustrated herein, although some or all of the instructions could be stored and/or executed elsewhere. In this example, the memory 22 optionally includes an intervention database 28 configured to store risk management interventions each associated with one or more risk issues, as described and illustrated in more detail later.

The communication interface 24 in the risk analyzing computing device 12 is optionally used to communicate between the risk analyzing computing device 12 and one or more of the medical practice computing device 16, and/or medical practice claims source database 14, which are all optionally connected together via the communication network(s) 18. By way of example only, the communication network(s) 18 can use TCP/IP over Ethernet and industry-standard protocols, including hypertext transfer protocol (HTTP) and/or secure HTTP (HTTPS), although other types and numbers of communication networks can be used.

The medical practice computing device 16 enables a user to provide condition indication data, including condition indications used by the associated medical practice in the treatment of patients, that can be uploaded or otherwise communicated to the risk analyzing computing device 12 using the communication network(s) 18, for example, as described and illustrated in more detail later. Accordingly, the medical practice computing device 16 can include a processor, a memory, and a communication interface, which are coupled together by a bus or other communication link, although other numbers and types of devices could be used in the medical practice computing device 16.

The medical malpractice claims source database 14 stores medical malpractice claims data for a plurality of liability insurance carriers. The medical malpractice claims data in this example includes condition indications associated with risk issues having corresponding risk indicators, as described and illustrated in more detail later. The medical malpractice claims source database 14 can be hosted by a server computing device that includes a processor, a memory, and a communication interface coupled together by a bus or other communication link, for example, although other numbers and types of devices could be used to store the medical malpractice claims source database 14.

Each of the risk analyzing computing device 12, medical practice computing device 16, and medical malpractice claims source database 14 can be implemented on any suitable computer apparatus or computing device. It is to be understood that the apparatuses and devices of the embodiments described herein are for exemplary purposes, as many variations of the specific hardware and software used to implement the embodiments are possible, as will be appreciated by those skilled in the relevant art(s).

The embodiments may also be implemented on computer apparatuses or devices that extend across any suitable network using any suitable interface mechanisms and communications technologies, including by way of example only telecommunications in any suitable form (e.g., voice and modem), wireless communications media, wireless communications networks, cellular communications networks, G3 communications networks, Public Switched Telephone Network (PSTNs), Packet Data Networks (PDNs), the Internet, intranets, and combinations thereof. Additionally, the communication network(s) in this example may employ any suitable interface mechanisms and network communication technologies including, for example, teletraffic in any suitable form (e.g., voice, modem, and the like), Public Switched Telephone Network (PSTNs), Ethernet-based Packet Data Networks (PDNs), combinations thereof, and the like.

The embodiments may also be embodied as one or more non-transitory computer readable media having instructions stored thereon for one or more aspects of this technology as described and illustrated by way of the embodiments herein, as described herein, which when executed by a processor, cause the processor to carry out the steps necessary to implement the methods of the embodiments, as described and illustrated herein.

Figure 2:
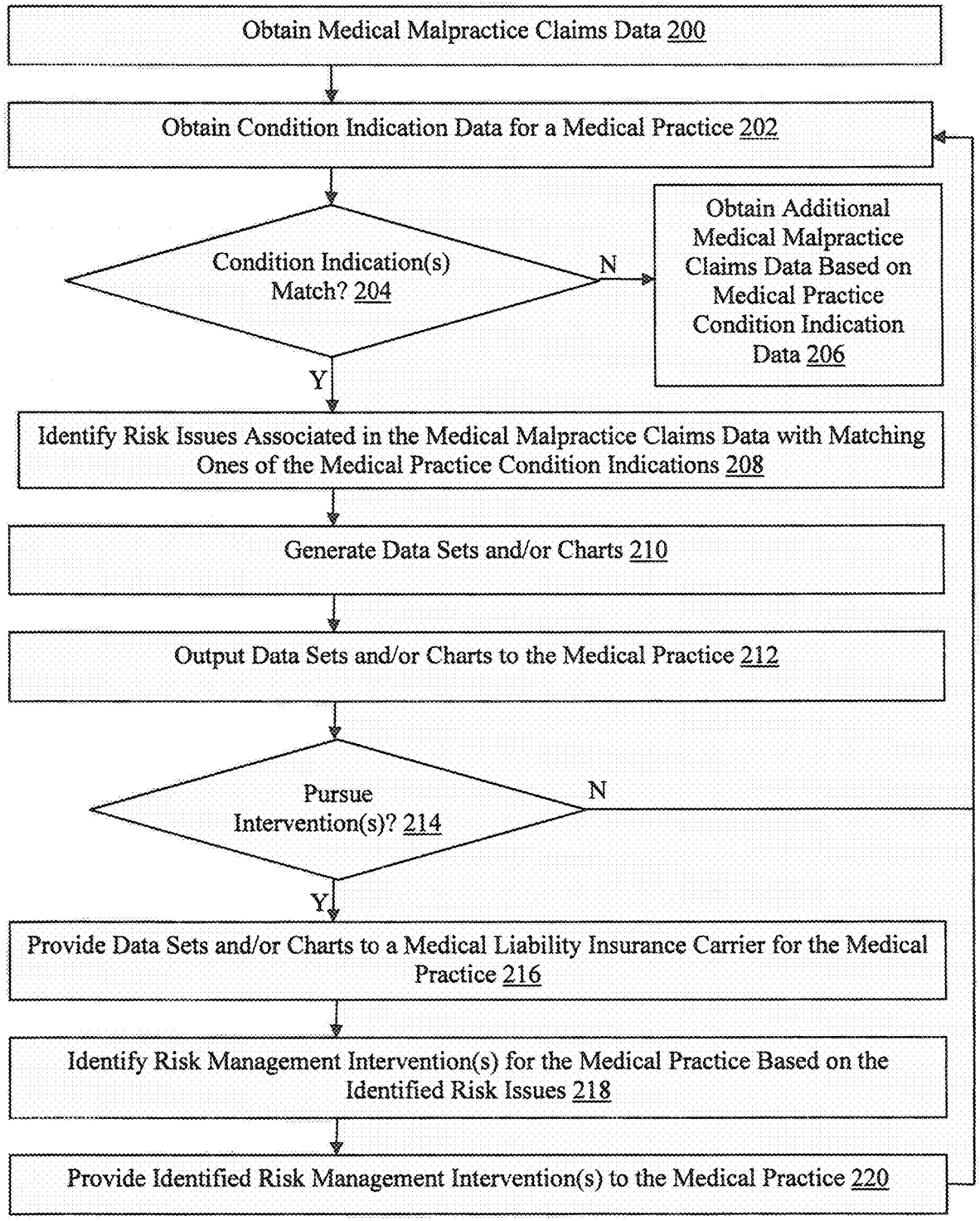
FIG. 2 is a flowchart of an exemplary method for generating risk management intervention recommendations for a medical practice.

An exemplary method for providing risk management analytics will now be described with reference to FIGS. 1-7. Referring more specifically to FIG. 2, a flow chart of an exemplary method for generating risk management intervention recommendations for a medical practice is illustrated. In this example, in step 200, medical malpractice claims data including risk issues associated with condition indications is obtained. In one example, the risk analyzing computing device 12 obtains the medical malpractice claims data from the medical malpractice claims source database 14, although the medical malpractice claims data can be obtained from other source in other examples.

In one example, the condition indications in the medical malpractice claims data in database 14 are International Statistical Classification of Diseases (ICD) codes (e.g., ICD-9 codes), although other types of standardized indications or codes can also be used. The condition indications are associated in the medical malpractice data with risk issues, which correspond to one or more risk indicators in this example, although the medical malpractice claims data can include other types and numbers of information. The medical malpractice data can be obtained from medical practices separately or as a set of aggregated data associated with a number of medical practices, such as available from PIAA, Inc. of Rockville, Md., for example.

In this example, the risk issues for a medical practice associated with the condition indications in the medical malpractice claims data can represent bases for medical malpractice claims, such as errors in diagnosis or X-ray errors, or procedures associated with treatment of a disease or condition that led to a malpractice claim, such as a magnetic resonance imaging (MRI) or computerized axial tomography (CAT) scan, for example, as described and illustrated in more detail later. Additionally, the risk indicators can include a percentage of insurance claims paid to close, an average indemnity cost, or an average cost for an insurance claim as a result of the risk issue, for example, although other risk indicators can also be used.

Optionally, the medical malpractice claims data can be filtered or obtained based on a type of medical practice (e.g., a radiology practice). Accordingly, in this example the condition indications in the medical malpractice claims data are associated in the medical malpractice claims data with a medial practice type. Additionally, the condition indications of the obtained medical malpractice claims data can be filtered or obtained based on ranking of the condition indications for a type of medical malpractice. The ranking can be based on frequency, number of malpractice claims, one or more of the risk indicators, or any other parameter(s).

Referring more specifically to FIG. 3, an exemplary table 300 of medical malpractice claims data from database 14 includes misadventure risk issues for the top ten condition indicators for a radiology type of medical practice is illustrated. In this example, one of the condition indications is a 786.5 ICD-9 code for unspecified chest pain, which is associated with two risk issues including errors in diagnosis and failure to supervise or monitor the case. In this example, the risk issues are misadventures or allegations of malpractice made by patients. Each risk issue is associated with one or more risk indicators, as described and illustrated in more detail later.

Referring back to FIG. 2, in step 202, condition indication data including condition indications associated with one medical practice are obtained. The condition indications obtained from the one medical practice can be ICD codes, for example, although other indications can also be used. Optionally, the condition indications can be obtained according to a predefined number (e.g., top ten) and a ranking of the condition indications based on use or frequency of the condition indications in the treatment of patients of the medical practice. In one example, a user of the medical practice computing device 16 can provide the condition indications to the risk analyzing computing device 12 over the communication network(s) 18, for example, such as by electronic mail. Other methods of obtaining the condition indications for the medical practice can also be used.

In step 204, the risk analyzing computing device 12 optionally determines whether there are comparable matches for the condition indications obtained for the one medical practice in the medical malpractice claims data obtained in step 200. In examples in which the medical malpractice claims data is obtained or filtered to include only a predefined number of condition indications (e.g., top ten) in step 200, there may not be exact correspondence with the condition indications in the predefined number of condition indications obtained for the medical practice in step 202.

Accordingly, if the risk analyzing computing device 12 determines that there are one or more condition indications obtained from the one medical practice that are not found in the obtained medical malpractice claims data, then the No branch is taken to step 206. In step 206, additional medical malpractice claims data is obtained, such as from the medical malpractice claims source database 14, corresponding to the one or more condition indications obtained from the one medical practice in step 202 not having a match in the medical malpractice claims data previously obtained in step 200.

Subsequent to step 206, or if the medical malpractice claims data is not limited to a predefined number in step 200 or there is sufficient correspondence between the predefined number of condition indications in the medical malpractice claims data and the condition indications obtained for the one medical practice in step 202 and the Yes branch is taken from step 204, the method proceeds to step 208. In step 208, the risk analyzing computing device 12 identifies, and optionally generates a new database including, risk issues associated in the medical malpractice claims data with matching ones of the condition indications associated with the one medical practice.

Optionally, the risk issues can be filtered in step 208 to include a subset of the risk issues corresponding to a highest one or more of the risk indicators or one or more of the risk indicators that exceeds a predefined threshold, for example, although other methods of filtering the risk issues can also be used. Referring back to FIG. 3, the errors in diagnosis risk issue corresponding to the condition indicator for headaches is associated with the highest average indemnity risk indicator. Additionally, the failure to supervise or monitor the case risk issue corresponding to the condition indicator for unspecific chest pains is associated with the highest average allocated loss adjustment expense (ALAE) or insurance claim cost. Accordingly, errors in diagnosis and/or failure to supervise or monitor the case risk issues can be identified in step 208 of FIG. 2.

Referring more specifically to FIG. 4, an exemplary table 400 of medical malpractice claims data including procedure risk issues for the top ten condition indicators for a radiology type of medical practice is illustrated. In this example, the CAT scan procedure can be identified in step 208 of FIG. 2 due to having the highest average indemnity risk indicator as associated with the condition indication for headaches and due to its association with more of the condition indications (3) than any other risk issue, for example. Additionally, in this example, the mammography procedure can be identified in step 208 of FIG. 2 due to having a relatively high (second highest) percentage of claims paid to close as compared to the other risk issues and a higher number of paid claims (95) than any other risk issue.

Referring more specifically to FIG. 5, an exemplary table 500 of medical malpractice claims data including legal risk issues for the top ten condition indicators for a radiology type of medical practice is illustrated. In this example, the vicarious liability, X-ray error, and problems with a patient's history, exam, or work-up risk issues can all be identified in step 208 of FIG. 2 due to having the three highest percentage paid to close risk indicators. Accordingly, risk issues in this example can include allegations bringing rise to medical malpractice claims, procedures associated with medical malpractice claims, or legal issues resulting in medical malpractice claims, although any other numbers and types of risk issues or bases for medical malpractice claims can also be used. Additionally, any other methods of identifying and optionally filtering the risk issues can also be used.

Referring back to FIG. 2, in step 210 the risk analyzing computing device 12 optionally generates data sets and/or charts based on the medical malpractice claims data and the condition indications obtained from the medical practice. These data sets and/or charts can be based on the predefined number of condition indications obtained or filtered from the medical malpractice claims data and the predefined number of condition indications obtained from the medical practice, for example. Accordingly, the data sets and charts correlate between the medical malpractice claims data and the medical practice condition indication data and optionally highlight or identify the areas of strongest correlation.

Figure 6:
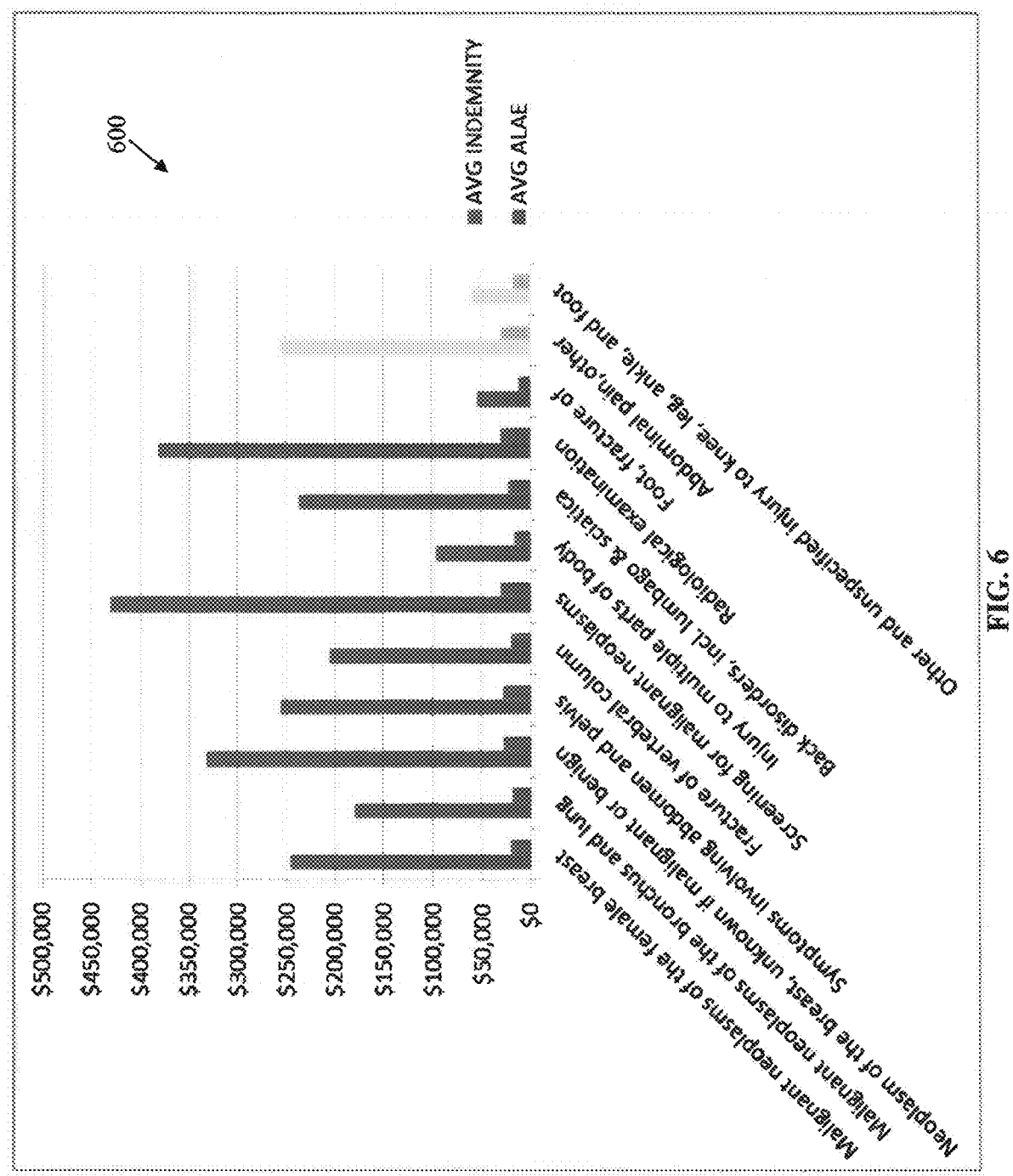
FIG. 6 is an exemplary chart with exemplary top condition indications for exemplary medical malpractice claims data associated with a radiology type of practice and exemplary condition indications for a radiology medical practice and associated average indemnity and average allocated loss adjustment expense.
Figure 7:
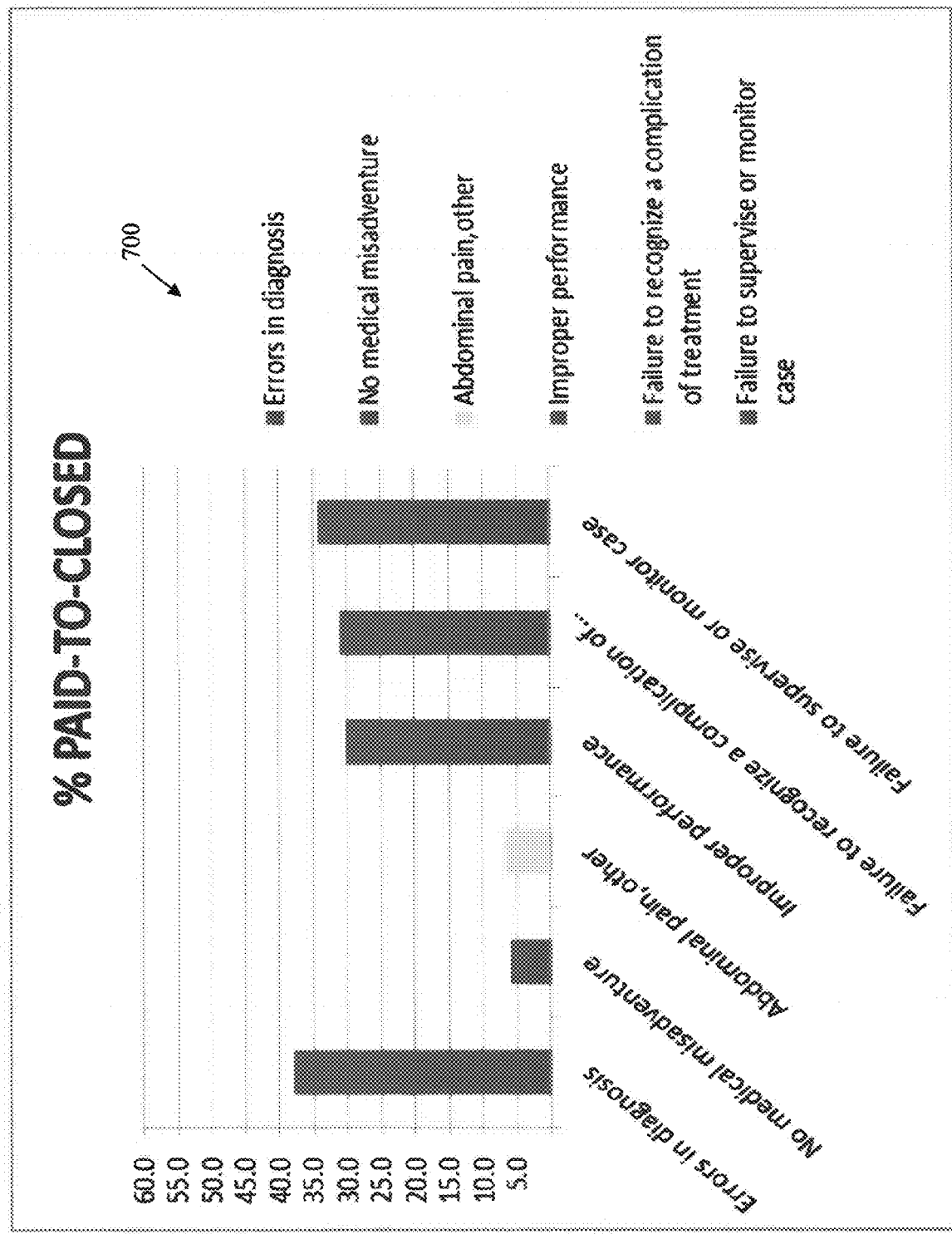
FIG. 7 is an exemplary chart with a portion of the exemplary top condition indications of the chart of FIG. 6 and associated percentage paid-to-close risk indicator.

Referring more specifically to FIG. 6, an exemplary chart 600 with exemplary top condition indications for exemplary medical malpractice claims data associated with a radiology type of practice and exemplary condition indications for a radiology medical practice and associated average indemnity and ALAE is illustrated. Referring more specifically to FIG. 7, an exemplary chart 700 with a portion of the exemplary top condition indications of the chart of FIG. 6 and associated percentage paid-to-close risk indicator is illustrated. In these examples, the condition indication associated with the "abdominal pain, other" condition compares to the condition indication for the medical practice and is therefore highlighted or illustrated in a different color. Additionally, other types and numbers of charts and/or data sets can be generated in step 210 of FIG. 2.

In step 212, the data sets and/or charts generated in the sixth step are provided to the medical practice. Accordingly, the risk analyzing computing device 12 can provide the generated data sets and/or charts by sending the data sets and/or charts to the medical practice computing device 16 using the communication network(s) 18. Alternatively, the risk analyzing computing device 12 can provide the generated data sets and/or charts by generating web page(s) including the data sets and/or charts that are made available to a user of the medical practice computing device 16 upon request, for example. In yet another alternative, the generated data sets and/or charts can be electronically mailed to the medical practice using the communication network(s) 18, for example. Other methods of providing the generated data sets and/or charts to the medical practice can also be used.

In step 214, a determination is made whether the medical practice has decided to pursue one or more risk management interventions. If the medical practice has decided not to pursue risk management intervention(s), then the No branch is taken back to step 202 and condition indication data is obtained for another medical practice, as described and illustrated in more detail earlier. Optionally, the No branch can be taken from step 214 back to step 200 and medical malpractice claims data can again be obtained if the most recently obtained medical malpractice claims data has become dated or a notification that new medical malpractice claims data is available has been received, for example.

However, referring back to step 214, if the medical practice has decided to pursue risk management intervention(s), then the Yes branch is taken to step 216. In step 216, the subset of the data sets and/or charts generated in step 210, for example, can be provided to a medical liability insurance carrier for the medical practice to identify possible risk management interventions for the conditions or procedures previously identified for the medical practice.

In step 218, the risk analyzing computing device 12 identifies risk management intervention(s) for the medical practice. In one example, the risk issues identified in step 208 are compared with the intervention database to identify recommended risk management interventions associated with the risk issues. The recommended risk management interventions can include patient safety initiatives, risk management programs, intervention tools, medical practice staff education, or any other type of risk management interventions.

In examples in which the insurance carrier is consulted in step 216, recommended risk management interventions can also be obtained from the insurance carrier based on the identified risk issues. In these examples, the risk management interventions obtained from the insurance carrier can be stored in the intervention database 28 and can be subsequently used to identify recommended risk management interventions in step 218, based on a comparison with the risk issues for another medical practice, as described and illustrated earlier, and without requiring interaction with another insurance carrier.

Accordingly, the risk management interventions recommended will be associated with the risk issues faced by the medical practice according to the medical malpractice claims data and based on the condition, procedure, or general risk indications associated with the treatment of patients by the medical practice. Other external sources of risk management interventions can also be used and other types and numbers of risk management interventions can also be identified in step 220.

In step 220, the identified recommended risk management intervention(s) are provided to the medical practice. The risk analyzing computing device 12 can provide the recommended risk management intervention(s) to the medical practice computing device in the form of a report and using the communication network(s) 18, for example. Alternatively, the risk analyzing computing device 12 can provide the recommended risk management intervention(s) by generating web page(s) that are made available to a user of the medical practice computing device 16 upon request, for example. In yet another example, the recommended intervention(s) can be provided by electronic mail or another form of communication using the communication network(s). Other methods of providing the recommended risk management intervention(s) to the medical practice can also be used.

Optionally, the provided recommended risk management intervention(s) can include timetables for implementing the recommended risk management intervention(s). Accordingly, the medical practice can implement the risk management intervention(s), optionally according to the timetable, and the practice, insurance carrier, or a third party, can monitor and/or measure the results with respect to increased patient safety. The medical practice can then discuss, based on the results of the monitoring and/or measuring, improved pay per performance with health payers as well as improved underwriting results and/or additional credits to the insurance premium with the medical practice's medical liability insurance carrier.

Accordingly, with this technology, medical practices can implement risk management interventions tailored to their practice and corresponding to risk issues associated with relevant condition indications, such as ICD codes. By using medical malpractice claims data for other medical practices that includes corresponding condition indications, risk issues can be identified that may be most appropriate for the medical practices with respect to risk management intervention(s) of those specialties. By implementing the recommended risk management intervention(s), medical practices can advantageously increase patient outcomes, improve pay for performance results, and reduce insurance costs.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. A method for improved risk management analytics to generate targeted risk management interventions and facilitate improved patient care, the method implemented by one or more risk analyzing computing devices and comprising:
   obtaining via one or more communication networks condition indication data associated with a plurality of medical practices and, from one or more remote medical malpractice claims source databases hosted by one or more server computing devices, medical malpractice claims data for a plurality of medical liability insurance carriers and for each of the plurality of medical practices:
      determining a frequency of occurrence of each of a plurality of International Statistical Classification of Diseases (ICD) codes in a portion of the condition indication data associated with the medical practice;
      generating a ranking of the ICD codes based on the frequency of occurrence, wherein the frequency of occurrence corresponds to a frequency of use of each of the ICD codes in the treatment of patients of the medical practice;
      comparing the portion of the condition indication data to the medical malpractice claims data to identify one or more of a plurality of risk issues correlated in the medical malpractice claims data with a subset of the ICD codes, wherein the subset of the ICD codes is determined based on the ranking and each of the risk issues corresponds with at least one basis for a medical malpractice claim in the medical malpractice claims data;
      retrieving one or more recommended risk management interventions from a local intervention database based on a correlation in the local intervention database of the one or more recommended risk management interventions with the identified one or more risk issues;
      generating one or more web pages comprising an indication of the one or more recommended risk management interventions and one or more charts comprising the one or more of the risk issues and generated based on a determined strength of a correlation between the portion of the condition indication data and the medical malpractice claims data, wherein at least one of the charts comprises a plurality of top condition indications in the medical malpractice claims data for a type of the medical practice and a portion of the medical malpractice claims data associated with each of the top condition indications, wherein at least one of the top condition indications corresponding to one of the subset of the ICD codes is graphically distinguishable from each of the other top condition indications in order to highlight one or more areas of strongest correlation; and
      providing the one or more web pages via the one or more communication networks in response to a request received from a medical practice computing device associated with the medical practice, and for electronic display on a display device of the medical practice computing device, to facilitate implementation of one or more of the recommended risk management interventions and resulting improved patient care.

2. The method of claim 1, wherein the medical malpractice claims data comprises another plurality of risk issues and each of the another plurality of risk issues corresponds to one or more risk indicator values selected from a percentage of insurance claims paid to close, an average indemnity cost, or an average cost for an insurance claim.

3. The method of claim 2, wherein the one or more of the another plurality of risk issues comprise a subset of the plurality of risk issues included in the medical malpractice claims data and correspond to a highest ranked one or more of the risk indicators or one or more of the risk indicators that exceeds a predefined threshold.

4. The method of claim 1, further comprising storing any of the recommended risk management interventions obtained from the medical liability insurance carriers in the intervention database as associated with a corresponding set of the risk issues.

5. A non-transitory computer readable medium having stored thereon instructions for improved risk management analytics to generate targeted risk management interventions and facilitate improved patient care comprising executable code which when executed by a processor, causes the processor to:
   obtain via one or more communication networks condition indication data associated with a plurality of medical practices and, from one or more remote medical malpractice claims source databases hosted by one or more server computing devices, medical malpractice claims data for a plurality of medical liability insurance carriers and for each of the plurality of medical practices:
      determine a frequency of occurrence of each of a plurality of International Statistical Classification of Diseases (ICD) codes in a portion of the condition indication data associated with the medical practice;
      generate a ranking of the ICD codes based on the frequency of occurrence, wherein the frequency of occurrence corresponds to a frequency of use of each of the ICD codes in the treatment of patients of the medical practice;
      compare the portion of the condition indication data to the medical malpractice claims data to identify one or more of a plurality of risk issues correlated in the medical malpractice claims data with a subset of the ICD codes, wherein the subset of the ICD codes is determined based on the ranking and each of the risk issues corresponds with at least one basis for a medical malpractice claim in the medical malpractice claims data;
      retrieve one or more recommended risk management interventions from a local intervention database based on a correlation in the local intervention database of the one or more recommended risk management interventions with the identified one or more risk issues;

generate one or more web pages comprising an indication of the one or more recommended risk management interventions and one or more charts comprising the one or more of the risk issues and generated based on a determined strength of a correlation between the portion of the condition indication data and the medical malpractice claims data, wherein at least one of the charts comprises a plurality of top condition indications in the medical malpractice claims data for a type of the medical practice and a portion of the medical malpractice claims data associated with each of the top condition indications, wherein at least one of the top condition indications corresponding to one of the subset of the ICD codes is graphically distinguishable from each of the other top condition indications in order to highlight one or more areas of strongest correlation; and provide the one or more web pages via the one or more communication networks in response to a request received from a medical practice computing device associated with the medical practice, and for electronic display on a display device of the medical practice computing device, to facilitate implementation of one or more of the recommended risk management interventions and resulting improved patient care.

6. The non-transitory computer readable medium of claim 5, wherein the medical malpractice claims data comprises another plurality of risk issues and each of the another plurality of risk issues corresponds to one or more risk indicator values selected from a percentage of insurance claims paid to close, an average indemnity cost, or an average cost for an insurance claim.

7. The non-transitory computer readable medium of claim 6, wherein the one or more of the another plurality of risk issues comprise a subset of the plurality of risk issues included in the medical malpractice claims data and correspond to a highest ranked one or more of the risk indicators or one or more of the risk indicators that exceeds a predefined threshold.

8. The non-transitory computer readable medium of claim 5, wherein the executable code, when executed by a processor, further causes the processor to store any of the recommended risk management interventions obtained from the medical liability insurance carriers in the intervention database as associated with a corresponding set of the risk issues.

9. A risk analyzing computing device, comprising a memory comprising programmed instructions stored thereon and at least one processor configured to execute the stored programmed instructions to:

obtain via one or more communication networks condition indication data associated with a plurality of medical practices and, from one or more remote medical malpractice claims source databases hosted by one or more server computing devices, medical malpractice claims data for a plurality of medical liability insurance carriers and for each of the plurality of medical practices:

determine a frequency of occurrence of each of a plurality of International Statistical Classification of Diseases (ICD) codes in a portion of the condition indication data associated with the medical practice;

generate a ranking of the ICD codes based on the frequency of occurrence, wherein the frequency of occurrence corresponds to a frequency of use of each of the ICD codes in the treatment of patients of the medical practice;

compare the portion of the condition indication data to the medical malpractice claims data to identify one or more of a plurality of risk issues correlated in the medical malpractice claims data with a subset of the ICD codes, wherein the subset of the ICD codes is determined based on the ranking and each of the risk issues corresponds with at least one basis for a medical malpractice claim in the medical malpractice claims data;

retrieve one or more recommended risk management interventions from a local intervention database based on a correlation in the local intervention database of the one or more recommended risk management interventions with the identified one or more risk issues;

generate one or more web pages comprising an indication of the one or more recommended risk management interventions and one or more charts comprising the one or more of the risk issues and generated based on a determined strength of a correlation between the portion of the condition indication data and the medical malpractice claims data, wherein at least one of the charts comprises a plurality of top condition indications in the medical malpractice claims data for a type of the medical practice and a portion of the medical malpractice claims data associated with each of the top condition indications, wherein at least one of the top condition indications corresponding to one of the subset of the ICD codes is graphically distinguishable from each of the other top condition indications in order to highlight one or more areas of strongest correlation; and provide the one or more web pages via the one or more communication networks in response to a request received from a medical practice computing device associated with the medical practice, and for electronic display on a display device of the medical practice computing device, to facilitate implementation of one or more of the recommended risk management interventions and resulting improved patient care.

10. The risk analyzing computing device of claim 9, wherein the medical malpractice claims data comprises another plurality of risk issues and each of the another plurality of risk issues corresponds to one or more risk indicator values selected from a percentage of insurance claims paid to close, an average indemnity cost, or an average cost for an insurance claim.

11. The risk analyzing computing device of claim 10, wherein the one or more of the another plurality of risk issues comprise a subset of the plurality of risk issues included in the medical malpractice claims data and correspond to a highest ranked one or more of the risk indicators or one or more of the risk indicators that exceeds a predefined threshold.

12. The risk analyzing computing device of claim 9, wherein the processor is further configured to execute the stored programmed instructions to store any of the recommended risk management interventions obtained from the medical liability insurance carriers in the intervention database as associated with a corresponding set of the risk issues.

* * * * *